United States Patent
Lee et al.

(10) Patent No.: US 7,964,754 B2
(45) Date of Patent: Jun. 21, 2011

(54) DIIMMONIUM SALT AND NEAR INFRARED RAY ABSORPTION FILM CONTAINING THE SAME

(75) Inventors: Min-Hyuk Lee, Seoul (KR); Ju-Sik Kang, Suwon-si (KR); Jeong-Ho Park, Suwon-si (KR); Sung-Yung Lee, Seoul (KR)

(73) Assignee: SK Chemicals Co., Ltd., Suwon-Si (KR)

( * ) Notice: Subject to any disclaimer, the term of this patent is extended or adjusted under 35 U.S.C. 154(b) by 341 days.

(21) Appl. No.: 12/440,188

(22) PCT Filed: Sep. 5, 2007

(86) PCT No.: PCT/KR2007/004289
§ 371 (c)(1),
(2), (4) Date: Mar. 5, 2009

(87) PCT Pub. No.: WO2008/030039
PCT Pub. Date: Mar. 13, 2008

(65) Prior Publication Data
US 2010/0179348 A1    Jul. 15, 2010

(30) Foreign Application Priority Data

Sep. 6, 2006    (KR) .................. 10-2006-0085529

(51) Int. Cl.
*C07C 251/22*    (2006.01)
*G06K 7/10*    (2006.01)
*G02B 5/22*    (2006.01)

(52) U.S. Cl. ........ 564/271; 564/199; 558/394; 359/350; 359/885

(58) Field of Classification Search .................. None
See application file for complete search history.

(56) References Cited

U.S. PATENT DOCUMENTS

| 6,475,590 B1 | 11/2002 | Kitayama et al. |
| 2005/0148786 A1 | 7/2005 | Ikeda et al. |
| 2006/0091365 A1 | 5/2006 | Kitayama et al. |

FOREIGN PATENT DOCUMENTS

| KR | 2001-0052783 A | 6/2001 |
| KR | 10-2004-0098749 B | 11/2004 |
| WO | WO-99/67200 A1 | 12/1999 |
| WO | WO-2004/068199 A1 | 8/2004 |

*Primary Examiner* — Brian J Davis
(74) *Attorney, Agent, or Firm* — Birch, Stewart, Kolasch & Birch, LLP

(57) ABSTRACT

Disclosed are a diimmonium salt and a near infrared ray absorption film including the same which is used for blocking the near infrared ray. The diimmonium salt for a near infrared ray absorption film is represented by Formula 1 of the specification, wherein, n is an integer of 1 or 2, $R_1$ to $R_8$ are independently a substituted or unsubstituted linear or branched $C_1$-$C_{10}$ alkyl group, the substituent for the alkyl group is selected from the group consisting of a cyano group, a nitro group, a carboxyl group, a sulfone group, a halogen atom, a hydroxyl group, a $C_1$-$C_8$ alkoxy, alkoxyalkoxy, acyloxy, or alkylamino group, and $C_6$-$C_{18}$ aryl or aryloxy group, and X is a substituted fluoro alkyl phosphate anion represented by Formula 2 of the specification, wherein, x is an integer of 0 or 1, y is an integer of 1, 2 or 3, z is an integer of 6-y, and $R_9$ to $R_{13}$ are independently a hydrogen atom (H) or a fluorine atom (F).

4 Claims, 1 Drawing Sheet

[Fig. 1]
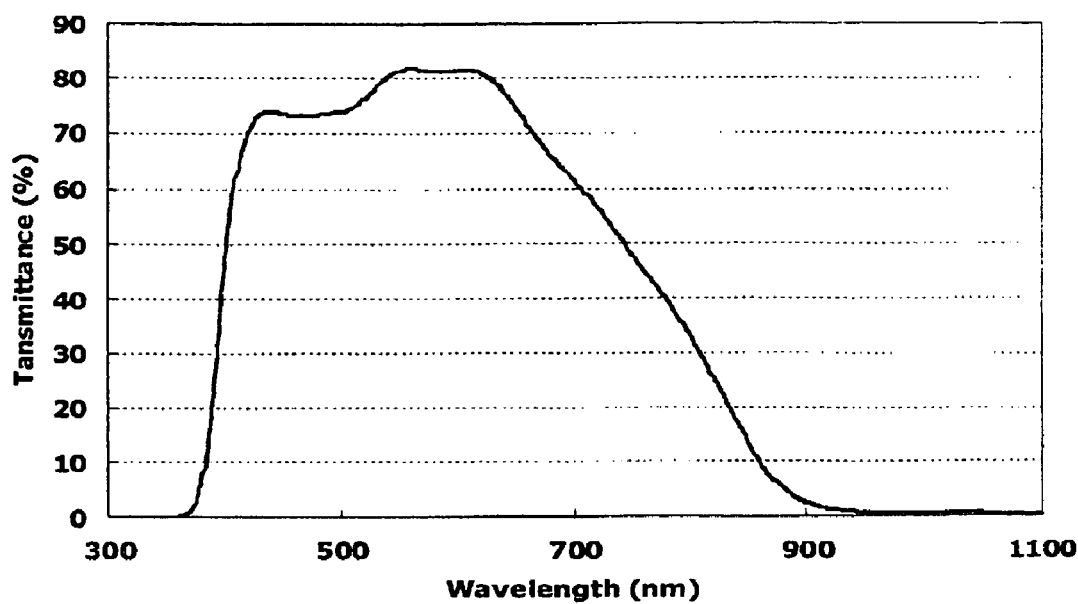

DIIMMONIUM SALT AND NEAR INFRARED RAY ABSORPTION FILM CONTAINING THE SAME

TECHNICAL FIELD

This invention relates to a compound for blocking near infrared ray, and more particularly, to a compound and a near infrared ray absorption film including the same, which can be used for a plasma display panel(PDP), an automobile glass, an architectural glass, and so on, in order to block the near infrared ray.

BACKGROUND ART

In the solar energy radiations, infrared radiation (ray) is most closely related to heat. The infrared rays can be classified into near infrared rays and far infrared rays. The near infrared rays are directly transmitted to the Earth from the Sun, and the far infrared rays include heat which is generated from various heating apparatus. The infra red ray has a longer wavelength than visible rays, and easily penetrates a material which blocks the visible rays. Accordingly, filters for blocking the near infrared rays are conventionally used for an automobile glass or an architectural glass for preventing the near infrared rays from being excessively transmitted into the interior of an automobile or a building.

Also, in a plasma display panel (PDP) which is recently developed for providing a large-size screen, electrodes for supplying signals and power are formed on the front glass panel of the PDP. Thus, during the operation of PDP, a lot of electromagnetic waves and a lot of near infrared rays are generated at the glass panel. The generated near infrared rays may induce mis-operations of a remote controller or an infrared ray communication port which utilizes infrared rays for data transmissions. Therefore, the filters for blocking the near infrared rays are conventionally used for the glass panel of the PDP.

Generally, a near infrared ray absorption film can be produced by coating the mixture of a near infrared ray absorption dye and a binder resin on a transparent film. The filter for blocking the near infrared ray (i.e. near infrared ray filter) can be produced by stacking several near infrared ray absorption films on a glass. The near infrared ray absorption film should have a good durability at high temperature or at high humidity atmosphere, and also should have a good light absorptivity at the wavelength of 800-1200 nm (near infrared ray region). The durability of the near infrared absorption film is determined by the difference between the first transmittance of a new absorption film and the second transmittance of the absorption film after exposing the absorption film during a predetermined time interval under the condition of high temperature or high humidity atmosphere. As the difference is smaller, the durability of the near infrared absorption film is better. The durability of the near infrared absorption film depends on the kinds of binder resin and the dye.

Conventionally, organic dyes, such as ammonium, aminium, diimmonium, quinone, phthalocyanine, naphthalocyanine, cyanine, and so on, are used for producing the near infrared ray absorption film. However, the conventional organic dyes, when used alone, have a weak durability to heat or light. Therefore, in Korean Patent No. 10-497149, a dithiol based metal complex dye having a good thermal stability is added to the conventional organic dye. However, the dithiol based metal complex dye is harmful to a human body since the metal complex dye contains heavy metals such as nickel, and the metal complex dye is not compatible with some organic dyes. In Korean Patent Laid-Open No. 2001-0052783, an inorganic monovalent ion (for example, hexafluoroantimonate, hexafluoroarsenate, hexafluorophosphonate, perclorate, or borofluoride) and an organic acid divalent anion (for example, trifluoromethane sulfonate or naphthalene disulfonate) are used for improving the heat-resistance and the light-resistance of a diimmonium compound. However, the inorganic monovalent ion and the organic acid divalent anion may contain toxic materials such as antimony or arsenic. Further, the inorganic monovalent ion and the organic acid divalent anion are weak to moisture or heat. Thus, the diimmonium salt can be decomposed, the absorptivity of the near infrared ray can be reduced, and, on the contrary, visible ray can be absorbed. To overcome these drawbacks, in U.S. Patent Application Publication No. 2005-148786, the anion of the diimmonium compound is replaced with sulfonimide based anion. However, there is a problem that some composition including the sulfonimide based salt is hydrolyzed at high temperature and high humidity atmosphere.

DISCLOSURE OF INVENTION

Technical Problem

It is an object of the present invention to provide a diimmonium salt for a near infrared ray absorption film having a good durability to light, heat and moisture.

It is other object of the present invention to provide a diimmonium salt for a near infrared ray absorption film which is not harmful to human body and has a good light absorption at the near infrared ray region.

It is another object of the present invention to provide a near infrared ray absorption film having a good durability at the environment of high temperature and high humidity atmosphere.

Technical Solution

In order to achieve these and other objects, the present invention provides a diimmonium salt for a near infrared ray absorption film represented by Formula 1.

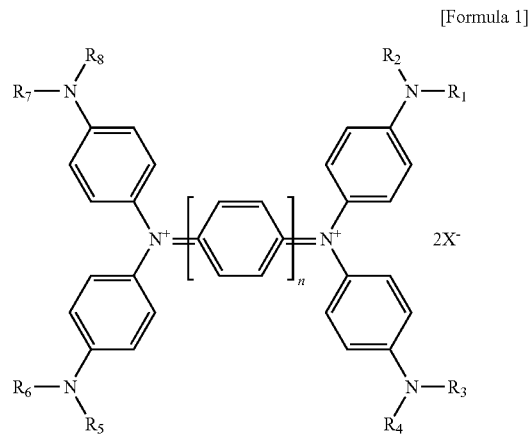

[Formula 1]

In Formula 1, n is an integer of 1 or 2, $R_1$ to $R_8$ are independently a substituted or unsubstituted linear or branched $C_1$-$C_{10}$ alkyl group. The substituent for the alkyl group includes a cyano group, a nitro group, a carboxyl group, a sulfone group, a halogen atom, a hydroxyl group, a $C_1$-$C_8$ alkoxy, alkoxyalkoxy, acyloxy, or alkylamino group, and $C_6$-$C_{18}$ aryl or aryloxy group. $X^-$ is a substituted fluoro alkyl phosphate anion represented by Formula 2.

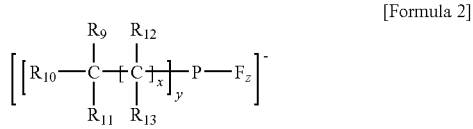
[Formula 2]

In Formula 2, x is an integer of 0 or 1, y is an integer of 1, 2 or 3, z is an integer of 6-y, and $R_9$ to $R_{13}$ are independently a hydrogen atom (H) or a fluorine atom (F).

The present invention also provides a near infrared ray absorption film containing the diimmonium salt represented by Formula 1.

BRIEF DESCRIPTION OF THE DRAWINGS

FIG. 1 is a UV spectrum showing the transmittance of a near infrared ray absorption film according to an embodiment of the present invention.

Mode for the Invention

A more complete appreciation of the invention, and many of the attendant advantages thereof, will be better appreciated by reference to the following detailed description.

Diimmonium salt for near infrared ray absorption film of the present invention is represented by Formula 1.

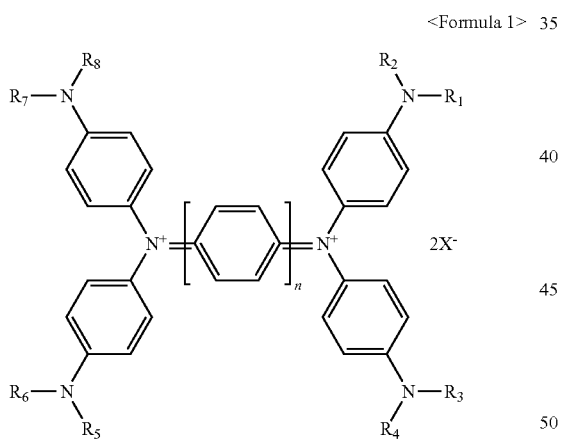
<Formula 1>

In Formula 1, n is an integer of 1 or 2, $R_1$ to $R_8$ are independently a substituted or unsubstituted linear or branched $C_1$-$C_{10}$ alkyl group. The substituent for the alkyl group includes a cyano group, a nitro group, a carboxyl group, a sulfone group, a halogen atom, a hydroxyl group, a $C_1$-$C_8$ alkoxy, alkoxyalkoxy, acyloxy, or alkylamino group, and $C_6$-$C_{18}$ aryl or aryloxy group. Preferably, the alkyl group includes methyl group, ethyl group, propyl group, butyl group, t-butyl group, and pentyl group. The halogen atom includes F, Cl, and Br. The alkoxy group includes methoxy group, ethoxy group, and isobutoxy group. The alkoxy alkoxy group includes methoxy ethoxy group. The acyloxy group includes acetyloxy group, butyryloxy group, hexylyloxy group and benzoyloxy group. The alkylamino group includes methylamino group and dimethylamino group. The aryl group includes phenyl group and naphthal group. The aryloxy group includes phenoxy group.

Preferable examples of a diimmonium cation composing the diimmonium salt of Formula 1 include N,N,N',N'-tetrakis{p-dimethylaminophenyl}-p-phenylenediamine, N,N,N',N'-tetrakis{p-diethylaminophenyl}-p-phenylenediamine, N,N,N',N'-tetrakis{p-di(n-butyl)aminophenyl}-p-phenylenediamine, N,N,N',N'-tetrakis{p-di(iso-butyl)aminophenyl}-p-phenylenediamine, N,N,N',N'-tetrakis{p-di(cyanopropyl)aminophenyl}-p-phenylenediamine, N,N,N',N'-tetrakis{p-di(2-hydroxyethyl)aminophenyl}-p-phenylenediamine, N,N,N',N'-tetrakis{p-dibenzylaminophenyl}-p-phenylenediamine, N,N,N',N'-tetrakis{p-di(1-naphthylmethyl)aminophenyl}-p-phenylenediamine, and N,N,N',N'-tetrakis{p-diacetylaminophenyl}-p-phenylenediamine.

$X^-$ of Formula 1 is a substituted fluoro alkyl phosphate anion represented by Formula 2.

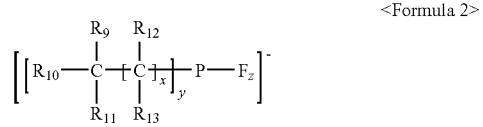
<Formula 2>

In Formula 2, x is an integer of 0 or 1, y is an integer of 1,2 or 3, z is an integer of 6-y, and $R_9$ to $R_{13}$ are independently a hydrogen atom (H) or a fluorine atom (F).

Preferably, at least one of $R_9$ to $R_{13}$ is a fluorine atom (F). Preferable examples of the substituted fluoro alkyl phosphate anion in Formula 2 include $[CF_3PF_5]^-$, $[(CF_3)_2PF_4]^-$, $[(CF_3)_3PF_3]^-$, $[C_2F_5PF_5]^-$, $[(C_2F_5)_2PF_4]^-$ and $[(C_2F_5)_3PF_3]^-$.

The diimmonium salt for a near infrared ray absorption film according to the present invention is a compound including fluoro alkyl phosphate anions and a diimmonium cation. The diimmonium salt can be prepared by reacting a diimmonium cation which is produced by oxidizing an amine compound of the following Formula 3 with a metal salt containing the fluoro alkyl phosphate anion of Formula 2.

The amine compound of Formula 3 can be produced with a conventional method. For example, firstly, Ullmann reaction of p-phenylenediamine and 1-chloro-4-nitrobenzene is carried out, and the produced reactant is reduced to prepare tetrakisaminophenyl-p-phenylenediamine. Then, the tetrakisaminophenyl-p-phenylenediamine is reacted with alkyl halogen compounds corresponding to $R_1$~$R_8$, which results in the preparation of the compound of Formula 3. For example, if $R_1$~$R_8$ of Formula 3 are n-$C_4H_9$, 8 mole of $BrC_4H_9$ can be used as the alkyl halogen compounds to prepare the compound of Formula 3. The reaction of the alkyl halogen compounds can be carried out in an organic solvent, preferably, in a water soluble polar solvent such as dimethylformamide (DMF), dimethylimidazolinone (DMI), n-methyl pyrrolidone (NMP), and so on, at the temperature of 30~160° C., preferably 50~140° C.,

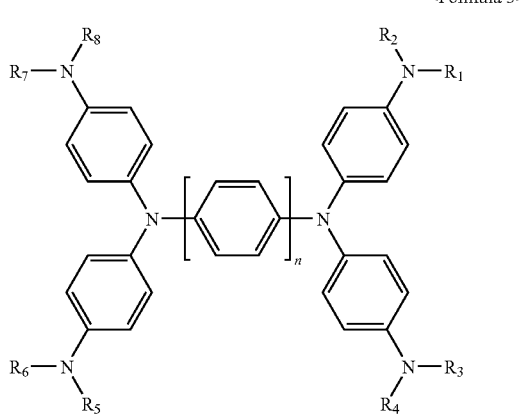

<Formula 3>

In Formula 3, n and $R_1$ to $R_8$ are as defined in Formula 1.

The metal salt containing the fluoro alkyl phosphate anion can be prepared with a conventional method, for example, which is disclosed in J. of General Chem. USSR, 59, 469-473, 1989, or Can. J. of Chem. 46, 1237-1248, 1968. For example, firstly, a phosphorane intermediate is prepared by using a phosphine compound such as $(CF_3)_3P$, $(CF_3)_2PCl$ or $CF_3PCl_2$ and sulfur tetrafluoride ($SF_4$). The produced phosphorane intermediate and cesium fluoride are dissolved with an active solvent such as acetonitrile, and then maintained for about 15 hours at room temperature. Thereafter, the excess cesium fluoride and the solvent are removed to obtain a cesium salt containing the fluoro alkyl phosphate anion of Formula 2. Alternatively, the phosphorane intermediate and water are reacted, and then reacted with silver oxide to prepare a phosphinate containing silver. The prepared phosphinate is reacted with $SF_4$ to produce a silver salt containing the fluoro alkyl phosphate anion. The obtained silver salt can be used as an oxidizing agent.

After producing the amine compound of Formula 3 and the metal salt containing the fluoro alkyl phosphate anion of Formula 2, the amine compound of Formula 3 is reacted with an oxidizing agent in a water soluble polar solvent such as dimethyl formamide (DMF), dimethylimidazolinone (DMI), n-methyl pyrrolidone (NMP) or so on to prepare the diimmonium cation. Then, the metal salt containing fluoro alkyl phosphate anion of Formula 2 is added thereto to carry out an ion exchange reaction, to prepare the diimmonium salt of Formula 1.

Examples of the oxidizing agent include silver nitrate, silver perchloric acid, copper nitrate etc. The amount of the oxidizing agent is the same to or more than the amount of the amine compound by mole. It is preferable that the mole ratio of the amine compound: the oxidizing agent is 1:2. The oxidation reaction can be carried out at the temperature of 0~100° C., preferably 30~70° C.

Alternatively, instead of the ion exchange reaction, the diimmonium salt of Formula 1 of the present invention can be prepared by directly reacting the amine compound of Formula 3 with the silver salt containing the fluoro alkyl phosphate anion of Formula 2. In this case, the silver salt works as an oxidization agent.

In the diimmonium salt of the present invention, the alkyl group of fluoro alkyl phosphate anion of Formula 2 is saturated with or includes fluorine atom(F). Thus, the diimmonium salt can be stably dissolved in a solvent, such as a halogen based solvent, an alcohol based solvent, a ketone based solvent, an ester based solvent, an aliphatic hydrocarbon based solvent, an aromatic hydrocarbon based solvent, an ether based solvent, and the mixtures thereof, even under the condition of high temperature and high humidity atmosphere.

In addition, as the number of fluorine atom(s) in the fluoro alkyl phosphate anion increases, the stability of the diimmonium salt of the present invention to moisture is improved. If the fluoro alkyl phosphate anion is completely saturated with fluorine, the diimmonium salt of the present invention does not absorb moisture, and becomes extremely stable. When the diimmonium salt of the present invention is stored in a dry solid state, the diimmonium salt is not decomposed at the temperature of less than 100° C., and have superior thermal stability.

The present invention also provides a near infrared ray absorption film containing the diimmonium salt represented by Formula 1.

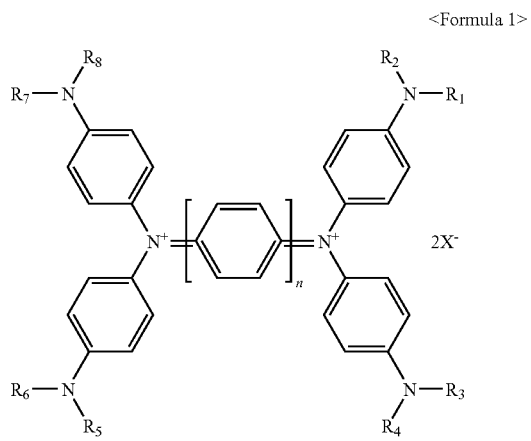

<Formula 1>

In Formula 1, n is an integer of 1 or 2, $R_1$ to $R_8$ are independently a substituted or unsubstituted linear or branched $C_1$-$C_{10}$ alkyl group. The substituent for the alkyl group includes a cyano group, a nitro group, a carboxyl group, a sulfone group, a halogen atom, a hydroxyl group, a $C_1$-$C_8$ alkoxy, alkoxyalkoxy, acyloxy, or alkylamino group, and $C_6$-$C_{18}$ aryl or aryloxy group. $X^-$ of Formula 1 is a substituted fluoro alkyl phosphate anion represented by Formula 2.

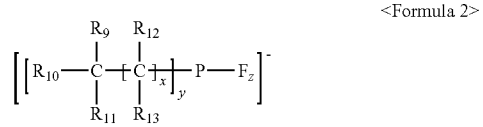

<Formula 2>

In Formula 2, x is an integer of 0 or 1, y is an integer of 1, 2 or 3, z is an integer of 6-y, and $R_9$ to $R_{13}$ are independently a hydrogen atom (H) or a fluorine atom (F).

Hereinafter, the method for preparing the near infrared ray absorption film of the present invention will be described.

First, a conventional binder resin such as polymethylmethacrylate, polyethylene terephthalate, polycarbonate, and so on, is dissolved with a conventional organic solvent such as methyl ethyl ketone, methyl isobutyl ketone, toluene, tetrahydrofuran, pentanone, 1,4-dioxane, and so on. Then, as a dye for absorbing the near infrared ray, the diimmonium salt is added to the binder resin solution to prepare a coating composition for the near infrared ray absorption film. Preferably, the amount of the diimmonium salt is 0.001 to 10 weight parts with respect to 100 weight parts of the binder resin solution, and the more preferable amount of the diimmonium salt is 0.01 to 1 weight parts. If the amount of the diimmonium salt is less than 0.001 weight parts, the near infrared ray absorption property of the film is not satisfactory. If the amount of the diimmonium salt is more than 10 weight parts, the transmittance of the visible rays may overly decrease. Next, the prepared coating composition for the near infrared ray absorption film is coated on a transparent film and dried, thereby forming the near infrared ray absorption film. The coating can be carried out by a conventional method, such as a spray coating, a roll coating, a bar coating, a spin coating, and so on. The coated composition can be dried, for example, by a hot-air drying method to remove the organic solvent.

Hereinafter, the preferable examples of the present invention and comparative examples are provided for better understanding of the present invention. The following examples are to illustrate the present invention, and the present invention is not limited by the following examples.

EXAMPLE 1

Synthesis of Diimmonium Salt

Step 1. Synthesis of tetrakisdibutylaminophenyl-p-phenylenediamine 95.2 g (0.2 mole) of N,N,N',N'-tetrakis(aminophenyl)-p-phenylenediamine, 548 g (4.0 mole) of 1-bromobutane and 330 g of anhydrous potassium carbonate were added to 800 g of dimethyl formamide (DMF). The reaction was carried out at 130° C. for 24 hours, and the reaction solution was cooled and filtered. 500□ of isopropyl alcohol was added to the filtered solution and stirred for 1 hour. After stirring, the produced compound was filtered, washed with methanol, and dried to obtain 96 g of the target product of brown color.

Step 2. Synthesis of cesium tris(trifluoromethyl)trifluorophosphate 30 g (0.1 mole) of tris(trifluoromethyl)phosphorus difluoride($(CF_3)_3PF_2$) and 30.4 g (0.2 mole) of cesium fluoride (CsF) were added to 200 ml of acetonitrile. The reaction was carried out at room temperature(25° C.) for 15 hours. After the completion of the reaction, the solvent in the reaction solution was distilled out under a reduced pressure. Water was added to the remaining brown materials to obtain an extract. The extract was freeze dried to produce 34 g of the target product of white color (Anal. C: 8.41%, F: 53.3%).

Step 3. Oxidation Reaction 18 g (0.02 mole) of tetrakisdibutylaminophenyl-p-phenylenediamine obtained in Step 1 and 6.8 g (0.04 mole) of silver nitrate were dissolved with 50 g of dimethyl formamide, and reacted at 60° C. for 30 minutes. After completion of the reaction, the precipitated silver was filtered, and 17.1 g (0.04 mole) of cesium tris(trifluoromethyl)trifluorophosphate obtained in Step 2 was added to the filtered solution and stirred for 30 minutes. Then, 100 ml of water was slowly added thereto to produce a precipitate. Next, the brown precipitate was filtered and washed with water, to obtain 28 g of the diimmonium salt (Anal. H: 7.6%, C: 66.2%, N: 4.7%, F: 18.8%, λmax: 1097 nm, molar absorption coefficient: 108,000, decomposition temperature: 262° C.).

EXAMPLE 2

Synthesis of Diimmonium Salt

Except for using 2-bromobutane instead of 1-bromobutane, the reactions were carried out in the same manner as described in Example 1 to produce 26 g of the diimmonium salt (Anal. H: 7.7%, C: 66.3%, N: 4.7%, F: 18.8%, λmax: 1102 nm, molar absorption coefficient: 103,000, decomposition temperature: 266° C.).

EXAMPLE 3

Preparation of Near Infrared Ray Absorption Film

Polymethylmethacrylate binder resin was dissolved with methyl ethyl ketone to prepare a 20 weight % binder resin solution. Then, the diimmonium salt prepared in Example 1 was added thereto so that the concentration of the diimmonium salt was 0.02%. The solution was uniformly mixed to prepare a coating composition for a near infrared ray absorption film. The prepared coating composition was coated on a transparent film (10□×10□) with the thickness of 3□ by using a bar coater to prepare the near infrared ray absorption film.

EXAMPLE 4

Preparation of Near Infrared Ray Absorption Film

Except for using the diimmonium salt prepared in Example 2 instead of the diimmonium salt prepared in Example 1, the near infrared ray absorption film was prepared in the same manner as described in Example 3.

COMPARATIVE EXAMPLE 1

Preparation of Near Infrared Ray Absorption Film

Except for using N,N,N',N'-tetrakis-[p-di(n-butyl)aminophenyl]-p-phenylenediimmonium trifluoromethyl sulfonyl imide instead of the diimmonium salt prepared in Example 1, the near infrared ray absorption film was prepared in the same manner as described in Example 3.

EXAMPLES 5, 6 and COMPARATIVE EXAMPLE 2

Evaluation of Transmittance

The transmittance of the near infrared ray absorption films prepared in Examples 3, 4 and Comparative Example 1 was measured with UV-VIS spectrometer at the near infrared ray region(850 nm) and the visible ray region (430 nm). The near infrared ray absorption films were exposed to a light source of 150 klux for 100 hours at 80% humidity and 100° C. by using a weathermeter (manufactured by SUGA SHIKENKI Co., Ltd.). The transmittance of the near infrared ray absorption films was measured again with the UV-VIS spectrometer, and the results are set forth in Table 1. FIG. 1 is a UV spectrum showing the transmittance of the near infrared ray absorption film prepared in Example 2.

TABLE 1

|  | Initial transmittance (%) | | Transmittance (%) after 100 hours | | Amount of change | |
| --- | --- | --- | --- | --- | --- | --- |
|  | 850 nm | 430 nm | 850 nm | 430 nm | 850 nm | 430 nm |
| Example 3 | 13.3 | 73.4 | 14.6 | 66.2 | 1.3 | 7.2 |
| Example 4 | 13.3 | 74.1 | 14.3 | 68.8 | 1.0 | 5.3 |
| Comparative Example 1 | 12.0 | 75.5 | 14.1 | 61.8 | 2.1 | 13.7 |

As shown in Table 1, the near infrared ray absorption film containing the fluoro alkyl phosphate anion according to the present invention (Examples 3 and 4) has a small transmittance change after the exposure to a high-humidity and high-temperature environment. In contrast, the near infrared ray absorption film of Comparative Example 1 has a large transmittance change. Thus, the near infrared ray absorption film of the present invention has superior durability to heat, moisture and light.

As descibed above, the diimmonium salt for the near infrared ray absorption film according to the present invention has superior durability to heat, moisture and light, is not harmful to a human body and has excellent light absorption at the near infrared ray region. In addition, the near infrared ray absorption film containing the diimmonium salt according to the present invention has good durability even under the high-humidity and high-temperature environment.

This application claims the priority benefit of Korean Patent Application No. 10-2006-0085529 filed on Sep. 6, 2006. All disclosure of the Korean Patent application is incorporated herein by reference.

The invention claimed is:

1. A diimmonium salt for a near infrared ray absorption film represented by Formula 1,

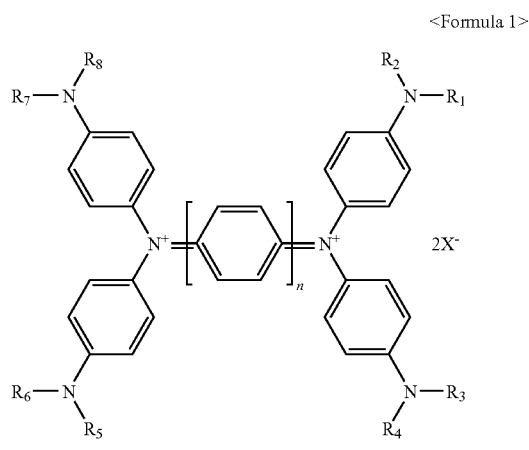

<Formula 1> wherein, n is an integer of 1 or 2, $R_1$ to $R_8$ are independently a substituted or un-substituted linear or branched $C_1$-$C_{10}$ alkyl group, the substituent for the alkyl group is selected from the group consisting of a cyano group, a nitro group, a carboxyl group, a sulfone group, a halogen atom, a hydroxyl group, a $C_1$-$C_8$ alkoxy, alkoxyalkoxy, acyloxy, or alkylamino group, and $C_6$-$C_{18}$ aryl or aryloxy group, and $X^-$ is a substituted fluoro alkyl phosphate anion represented by Formula 2,

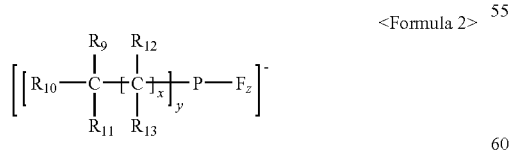

<Formula 2> wherein, x is an integer of 0 or 1, y is an integer of 1, 2 or 3, z is an integer of 6-y, and $R_9$ to $R_{13}$ are independently a hydrogen atom (H) or a fluorine atom (F).

2. The diimmonium salt according to claim 1, wherein a diimmonium cation of the diimmonium salt is selected from the group consisting of N,N,N',N'-tetrakis{p-dimethylaminophenyl}-p-phenylenediamine,
N,N,N',N'-tetrakis{p-diethylaminophenyl}-p-phenylenediamine,
N,N,N',N'-tetrakis{p-di(n-butyl)aminophenyl}-p-phenylenediamine,
N,N,N',N'-tetrakis{p-di(iso-butyl)aminophenyl}-p-phenylenediamine,
N,N,N',N'-tetrakis{p-di(cyanopropyl)aminophenyl}-p-phenylenediamine,
N,N,N',N'-tetrakis{p-di(2-hydroxyethyl)aminophenyl}-p-phenylenediamine,
N,N,N',N'-tetrakis{p-dibenzylaminophenyl}-p-phenylenediamine,
N,N,N',N'-tetrakis{p-di(1-naphthylmethyl)aminophenyl}-p-phenylenediamine,
and N,N,N',N'-tetrakis{p-diacetylaminophenyl}-p-phenylenediamine.

3. The diimmonium salt according to claim 1, wherein the fluoro alkyl phosphate anion is selected from the group consisting of $[CF_3PF_5]^-$, $[(CF_3)_2PF_4]^-$, $[(CF_3)_3PF_3]^-$, $[C_2F_5PF_5]^-$, $[(C_2F_5)_2PF_4]^-$ and $[(C_2F_5)_3PF_3]^-$.

4. A near infrared ray absorption film containing the diimmonium salt represented by Formula 1.

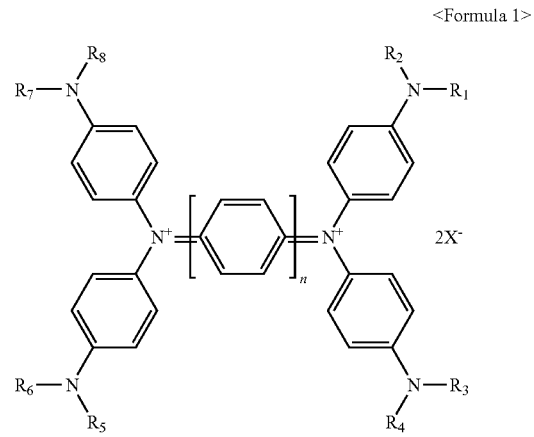

<Formula 1> wherein, n is an integer of 1 or 2, $R_1$ to $R_8$ are independently a substituted or unsubstituted linear or branched $C_1$-$C_{10}$ alkyl group, the substituent for the alkyl group is selected from the group consisting of a cyano group, a nitro group, a carboxyl group, a sulfone group, a halogen atom, a hydroxyl group, a $C_1$-$C_8$ alkoxy, alkoxyalkoxy, acyloxy, or alkylamino group, and $C_6$-$C_{18}$ aryl or aryloxy group, and $X^-$ is a substituted fluoro alkyl phosphate anion represented by Formula 2,

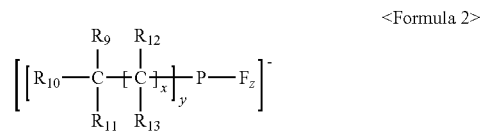

<Formula 2> wherein, x is an integer of 0 or 1, y is an integer of 1, 2 or 3, z is an integer of 6-y, and $R_9$ to $R_{13}$ are independently a hydrogen atom (H) or a fluorine atom (F).

* * * * *